United States Patent [19]

Morman

[11] Patent Number: 5,611,879
[45] Date of Patent: Mar. 18, 1997

[54] ABSORBENT ARTICLE HAVING AN ABSORBENT WITH A VARIABLE DENSITY IN THE Z DIRECTION AND A METHOD OF FORMING SAID ARTICLE

[75] Inventor: Michael T. Morman, Alpharetta, Ga.

[73] Assignee: Kimberly-Clark Corporation, Neenah, Wis.

[21] Appl. No.: 685,585

[22] Filed: Apr. 15, 1991

Related U.S. Application Data

[63] Continuation-in-part of Ser. No. 595,055, Oct. 9, 1990, abandoned, which is a continuation-in-part of Ser. No. 136,171, Dec. 18, 1987, abandoned.

[51] Int. Cl.⁶ .............................. B31F 1/00; B32B 31/20; B29C 49/00
[52] U.S. Cl. .......................... 156/201; 156/204; 156/209; 156/308.4; 156/309.1; 264/284; 604/6; 604/380; 604/382
[58] Field of Search ...................................... 604/368, 376, 604/365, 366, 378–384, 385.1, 370, 774, 375, 387; 156/201, 308.2, 204, 209, 308.4, 301.6; 428/121, 130, 156, 170, 212, 213, 215, 216, 218, 220; 264/284

[56] References Cited

U.S. PATENT DOCUMENTS

| | | | |
|---|---|---|---|
| 2,296,341 | 9/1942 | Fourness | 128/290 |
| 2,787,271 | 4/1957 | Clark | 128/290 |
| 2,952,259 | 9/1960 | Burgeni | 128/290 |
| 2,952,260 | 9/1960 | Burgeni | 128/290 |
| 3,017,304 | 1/1962 | Burgeni | 154/54 |
| 3,430,629 | 3/1969 | Murphy | 128/284 |
| 3,654,929 | 4/1972 | Nilssen et al. | 604/378 |
| 3,667,468 | 6/1972 | Nystrand et al. | 128/290 |
| 3,699,966 | 10/1972 | Chapuis | 128/290 R |
| 3,779,246 | 12/1973 | Mesek et al. | 128/287 |
| 3,858,585 | 1/1975 | Chatterjee | 128/290 R |
| 3,860,002 | 1/1975 | Kolbach | 128/284 |
| 3,897,784 | 8/1975 | Fitzgerald | 604/380 |
| 3,900,027 | 8/1975 | Keedwell | 128/268 |
| 3,901,238 | 8/1979 | Gellert et al. | 604/390 |
| 3,938,522 | 2/1976 | Repke | 128/287 |
| 4,029,101 | 6/1977 | Chesky et al. | 128/290 R |
| 4,045,833 | 9/1977 | Mesek et al. | 5/335 |
| 4,100,324 | 7/1978 | Anderson et al. | 428/288 |
| 4,223,677 | 9/1980 | Anderson | 128/287 |
| 4,226,237 | 10/1980 | Levesque | 128/285 |
| 4,232,674 | 11/1980 | Melican | 604/378 |
| 4,315,507 | 2/1982 | Whitehead et al. | 128/287 |
| 4,315,965 | 2/1982 | Mason et al. | 428/198 |
| 4,377,615 | 3/1983 | Suzuki et al. | 428/213 |
| 4,417,893 | 11/1983 | Mizutani et al. | 604/366 |
| 4,449,979 | 5/1984 | Holtman | 604/379 |
| 4,475,913 | 10/1984 | Hlaban | 604/387 |
| 4,496,358 | 1/1985 | Karami et al. | 604/379 |

(List continued on next page.)

FOREIGN PATENT DOCUMENTS

| | | |
|---|---|---|
| 2163295 | 7/1972 | Germany. |
| 3620077A1 | 12/1987 | Germany. |
| 2113731 | 8/1983 | United Kingdom. |
| 2254255 | 10/1992 | United Kingdom. |
| WO92/11830 | 7/1992 | WIPO. |

*Primary Examiner*—David Isabella
*Assistant Examiner*—K. M. Reiche
*Attorney, Agent, or Firm*—Thomas J. Connelly

[57] ABSTRACT

An absorbent article, such as a sanitary napkin, a diaper, training pants, an incontinent garment or a bedpad is disclosed for absorption of human exudate. The absorbent article includes an absorbent having a homogeneous composition with an essentially constant density in the x-y plane. The absorbent has at least two distinct portions which are integrally joined together by a junction line and each portion has a thickness different from an adjacent portion. The absorbent is folded on the junction line to obtain a variable density along the z axis. The folded absorbent also has a uniform capillary size in the x-y plane and a variable capillary size in the z direction. The absorbent article further includes a liquid-permeable cover which is positioned adjacent to at least one surface of the absorbent. A method of forming the article is also disclosed.

1 Claim, 6 Drawing Sheets

U.S. PATENT DOCUMENTS

| | | | |
|---|---|---|---|
| 4,501,586 | 2/1985 | Holtman | 604/380 |
| 4,505,705 | 3/1985 | Matthews et al. | 604/385 |
| 4,557,777 | 12/1985 | Sabee | 156/201 |
| 4,560,379 | 12/1985 | Stemmler | 604/385 |
| 4,576,596 | 3/1986 | Jackson et al. | 604/370 |
| 4,590,114 | 5/1986 | Holtman | 604/371 |
| 4,604,313 | 8/1986 | McFarland et al. | 428/172 |
| 4,650,480 | 3/1987 | Stemmler | 604/368 |
| 4,818,315 | 4/1989 | Hellgren et al. | 156/62.2 |

ABSORBENT ARTICLE HAVING AN ABSORBENT WITH A VARIABLE DENSITY IN THE Z DIRECTION AND A METHOD OF FORMING SAID ARTICLE

The present application U.S. Ser. No. 07/685,585 filed Apr. 15, 1991, is a continuation-in-part of U.S. Ser. No. 07/595,055 filed Oct. 9, 1990, now abandoned, which, in turn, is a continuation-in-part of U.S. Ser. No. 07/136,171 filed Dec. 18, 1987, which is now abandoned.

FIELD OF THE INVENTION

This invention relates to an absorbent article, such as a sanitary napkin, a diaper, training pants, an incontinent garment or a bedpad, having an absorbent with a variable density in the z direction. A method of forming the article is also disclosed.

BACKGROUND OF THE INVENTION

Absorbent pads such as sanitary napkins which utilize cellulosic fiber as their principal absorbent are well known. Cellulosic fiber provides a relatively inexpensive source of absorbent material but suffers from distinct disadvantages when utilized alone as an absorbent layer. One of the main disadvantages is that when a layer of cellulosic fiber is wetted, it tends to collapse upon itself. This results in a saturated cellulosic fiber which is dense, compacted, and relatively hard and uncomfortable.

It has been proposed that sanitary napkins be formed of a material containing plastic fibers that allow fusing the absorbent to aid in shaping. Such a pad having a C-fold structure has been proposed in U.S. Pat. No. 4,576,596 issued to Jackson et al. The Jackson patent also teaches that an insert, such as a meltblown strip, may be incorporated into the interior of the sanitary napkin to aid in absorbing and holding body fluids. While such a sanitary napkin is satisfactory, the thermoplastic-containing absorbent has properties that are a compromise between softness, stiffness, fluid transfer and fluid holding properties.

It is desirable that the absorbent material at the top of a feminine pad, adjacent to the wearer's body, be soft and cushiony. The absorbent material should also be high in porosity, that is, it should have a low density to facilitate rapid fluid absorption and be capable of transferring the fluid rapidly away from the body. The absorbent material situated below the top absorbent should have good fluid holding properties and be capable of wicking the fluid throughout the pad. These desirable features are not present in the Jackson patent.

Other U.S. patents, such as U.S. Pat. Nos. 4,505,705; 4,475,913; 3,699,966 and 3,430,629, teach that the absorbent can be folded about itself without referring to the advantages of having a variable density in the z direction. Still other U.S. patents, such as U.S. Pat. Nos. 3,017,304; 3,779,246; 4,226,237; 4,377,615 and 4,223,677, teach the use of various layers of absorbents having different thicknesses and densities. They do not suggest the use of a single absorbent sheet which is folded upon itself.

There are other U.S. patents, such as U.S. Pat. Nos. 4,496,358; 4,449,979 and 3,900,027, which teach the advantages of having a variable density in the z direction. However, no mention is made of folding the absorbent material. Lastly, U.S. Pat. No. 4,315,507 issued to Whitehead teaches forming a fusible baffle on one surface of an absorbent which is then used in a sanitary napkin. However, the baffle is completely covered by an outer wrap and, therefore, does not have an external surface which contacts the undergarment.

Another compromise in single absorbency pads is strength. Generally, an absorbent that has a higher density is stiffer and can prevent bending and twisting of the pad while in use. However, a dense absorbent will not feel as soft to the wearer and, therefore, sacrifices comfort in order to achieve stiffness.

Feminine pads having multiple layers of different densities have also been proposed. However, such pads are expensive and complicated to manufacture as they require formation and uniting of several different absorbent materials with good alignment at high speed and low cost. Accordingly, there is a need for an absorbent article which has a soft feel and which has a variable density in the z direction.

SUMMARY OF THE INVENTION

Briefly, this invention relates to absorbent articles such as sanitary napkins, diapers, training pants, incontinence garments, bedpads, etc. which are designed for absorption of human exudate. The absorbent article includes an absorbent having a homogeneous composition which has a constant density in any plane aligned perpendicular to the z direction. The absorbent also has at least two distinct portions which are integrally joined together by a junction line, and each portion has a thickness different from an adjacent portion. The absorbent is folded upon itself, to obtain a variable density in the z direction. The folded absorbent has a uniform capillary size in any plane aligned perpendicular to the z direction and a variable capillary size in the z direction. The method of forming the article is also disclosed.

The general object of this invention is to provide an absorbent article having a folded absorbent with a variable density in the z direction. A more specific object of this invention is to provide an absorbent article with a folded absorbent having a homogeneous composition and having a constant density in any plane aligned perpendicular to the z direction.

Another object of this invention is to provide an absorbent article which is soft and comfortable while having good liquid holding properties.

A further object of this invention is to provide a simple method of manufacturing an absorbent article.

Still another object of this invention is to provide an economical method of forming an absorbent article having an absorbent with a variable density in the z direction.

Other objects and advantages of the present invention will become apparent to those skilled in the art in view of the following description and the accompanying drawings.

DETAILED DESCRIPTION OF THE PREFERRED EMBODIMENTS

Figure 1:
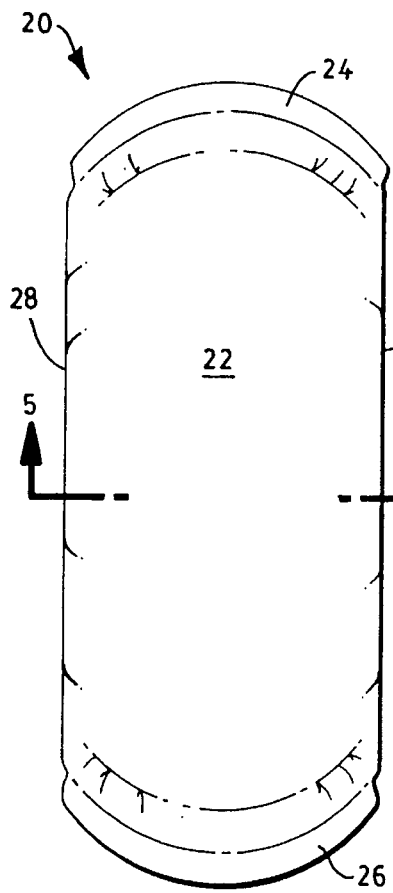
FIG. 1 is a top view of an absorbent pad.
Figure 2:
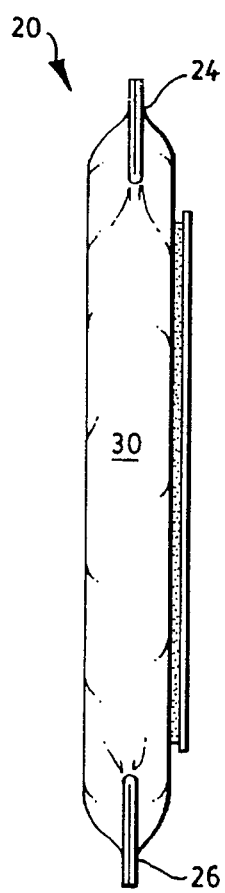
FIG. 2 is a side view of the absorbent pad shown in FIG. 1.
Figure 3:
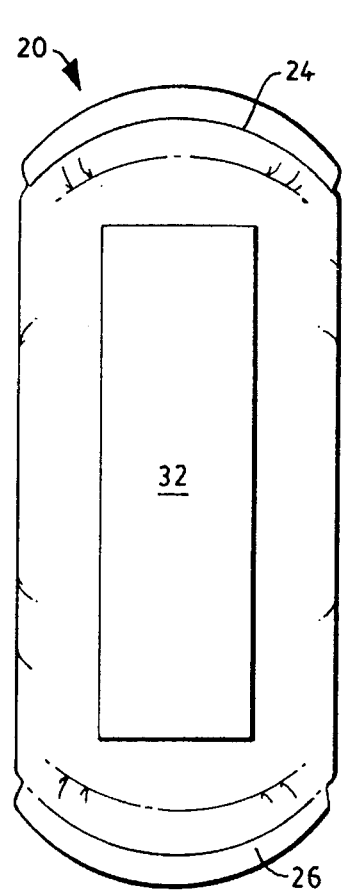
FIG. 3 is a bottom view of the absorbent pad shown in FIG. 1.
Figure 4:
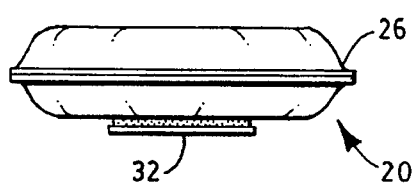
FIG. 4 is an end view of the absorbent pad shown in FIG. 1.
Figure 5:
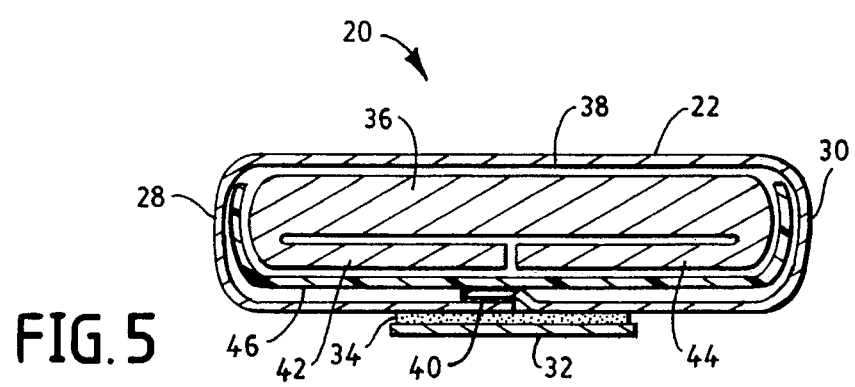
FIG. 5 is the cross-sectional view of FIG. 1 taken along line 5—5 of FIG. 1.

Referring to FIGS. 1–5, an absorbent article 20 in the shape of a sanitary napkin is shown. It should be noted that the absorbent article can also be a diaper, training pants, an incontinent garment, a bedpad, etc. The absorbent article 20 includes a bodyside surface 22, a garment-facing surface 23, distal ends seals 24 and 26 and a pair of longitudinally extending sides 28 and 30. The article further includes an absorbent 35, a liquid-permeable cover 38 and a liquid-impermeable baffle 46. The absorbent 35 is an integral sheet of absorbent material which has a homogeneous composition. The absorbent 35 has an essentially constant density in any plane aligned perpendicular to the z direction and is folded upon itself to have a variable density in the z direction. The x and y directions refer to the length and width of the product and the z direction refers to the thickness of the product. The folded absorbent 35 also has a uniform capillary size in plane aligned perpendicular to the z direction and a variable capillary size in the z direction. The capillary size in the z direction can vary from large to small as one goes from the top to the bottom of the absorbent. The capillary size can also be altered so that the smaller sized capillaries are located in the center of the absorbent. The variable density can be obtained by compressing one or more portions of the absorbent 35 and then folding these portions relative to one or more noncompressed or less compressed portions as shown in FIG. 5. The compressed portions are generally thinner in thickness than the noncompressed or less compressed portions. Generally, for an initially homogeneous absorbent, the thickness decreases as the density increases. The compressed portions are attached to the noncompressed or less compressed portions by one or more junction lines (A). The junction lines (A) provide a good location for folding one portion relative to an adjacent portion.

The absorbent 35 can contain thermoplastic polymers which can be permanently deformed by the application of heat and pressure. Such materials include polypropylene, nylon, polyethylene, polyesters, etc. Typical of such materials are bonded carded webs, meltblown and spunbond fabrics. Composites with a low temperature melting component, which can be fused during compression and which also have a high melting temperature or non-melting component for structural integrity, are especially good. A preferred material is coform. Coform is an air-formed blend of meltblown fibers and staple and/or pulp fibers. The formation of such material is disclosed in U.S. Pat. No. 4,100,324 issued to Anderson et al. It is also possible to add a high absorbency polymeric material, i.e. "superabsorbent", to the coform as suggested by British patent application No. 2,113,731 to Minto et al. and by U.S. Pat. No. 4,604,313 issued to McFarland et al. Coform formed from polypropylene meltblown and wood fibers, with or without superabsorbent particles, is preferred. Coform can be readily heatset at low temperatures, has good absorbency characteristics and is low in cost.

Referring to FIG. 5, the absorbent 35 consist of a noncompressed portion 36 positioned adjacent to the liquid-permeable cover 38 and two compressed portions 42 and 44 positioned therebelow. The noncompressed portion 36 is softer and has a lower density than the compressed portions 42 and 44. The noncompressed portion 36 is designed to quickly absorb body fluid which is discharged onto the sanitary napkin 20 and transfers it downward into the compressed portions 42 and 44. The dense compressed portions 42 and 44 are capable of retaining the body fluid and can keep it away from the skin of the user. This creates a dry feel at the bodyside surface 22 of the absorbent article 20 which is very desirable to the ultimate user. The compressed portions 42 and 44 have the ability to resist giving up the body fluid should they be compressed further by body movement. The compressed portions 42 and 44 also provide strength and rigidity to the absorbent article 20.

In FIG. 5, the liquid-impermeable baffle 46 is positioned below the compressed portions 42 and 44 of the absorbent 35 and extends upward along the longitudinally extending sides 28 and 30 of the article 20. The baffle 46 prevents passage of body fluid from the absorbent 35 to the adjacent undergarment of the wearer. The baffle 46 can be constructed from any liquid-impermeable material. Two preferred materials include polyethylene and polypropylene which can be formed as very thin films. These two materials are relatively low in cost and are quiet when worn.

The liquid-permeable cover 38 wraps around the absorbent 35 and the baffle 46 and can be overlapped upon itself on the garment-facing surface 23. The overlap can be secured by an adhesive 40. The ends of the cover 38 are sealed at a location where the absorbent 35 is not present, such as by an ultrasonic seal, to form the end seals 24 and 26. The cover 38 should be constructed from a material which will allow rapid passage of body fluid therethrough. Suitable materials include perforated films, woven materials and tissue. A preferred material is a polypropylene spunbond material because it has good strength, is comfortable and passes fluids easily.

The garment-facing surface 23 is provided with a removable peel strip 32 that is intended to be removed prior to use.

By removing the peel strip 32, a garment attachment adhesive 34 is exposed which is designed to provide a means for attaching the absorbent article 20 to the inner crotch portion of an undergarment.

Figure 6:
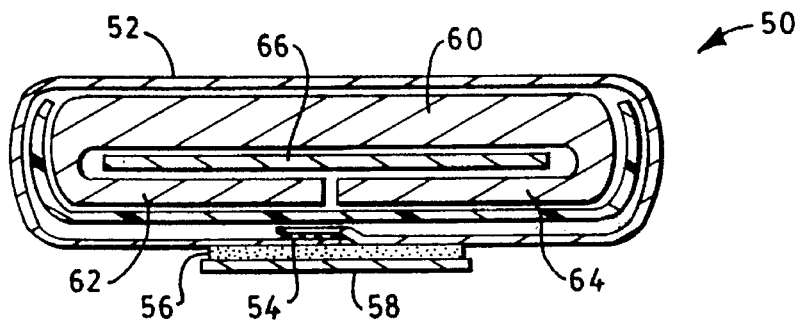
FIG. 6 is a cross-sectional view of an alternative embodiment of the absorbent pad.

Referring to FIG. 6, an alternative absorbent article 50, in the form of a sanitary napkin, is shown. The absorbent article 50 includes a liquid-permeable cover 52, a liquid-impermeable baffle 53 and an absorbent 55. The cover 52 is overlapped upon itself on the garment-facing side and is joined together by a construction adhesive 54. A garment attachment adhesive 56 is secured to the exterior surface of the cover 52 approximate the overlap and, in turn, is covered by a removable peel strip 58. Enclosed within the cover 52 is the absorbent 55 which includes a noncompressed portion 60 and compressed portions 62 and 64. Preferably, the absorbent 55 is folded along two spaced-apart junction lines (A) which are aligned with the axis of thickness change. The folded absorbent 55 is situated such that the noncompressed portion 60 is positioned adjacent to the cover 52 and the compressed portions 62 and 64 are C-folded beneath the noncompressed portion 60. The compressed portions 62 and 64 have a greater density than the noncompressed portion. It should be noted that the noncompressed portion 60 can be slightly compressed if desired, but that it should still have a lesser density than the compressed portions 62 and 64. A transfer layer 66 is positioned between the noncompressed portion 60 and the compressed portions 62 and 64. The transfer layer 66 can be a strip of meltblown polymer which has the ability to retain body fluid and transfer the fluid longitudinally and traversely along its length and width.

Figure 7:
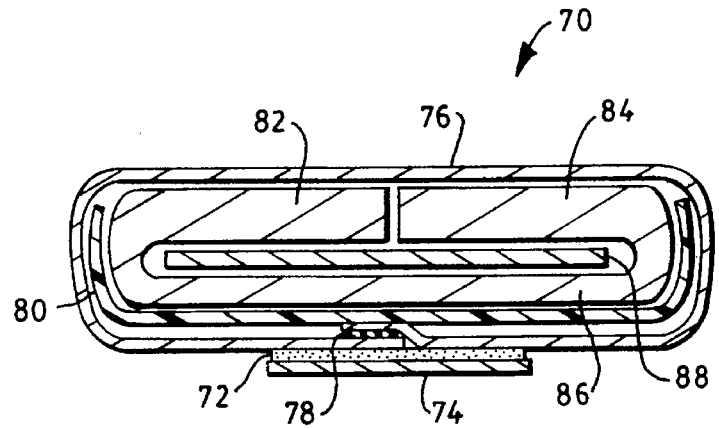
FIG. 7 is a cross-sectional view of another alternative embodiment of the absorbent pad.

Referring to FIG. 7, another embodiment of an absorbent article 70, in the form of a sanitary napkin, is shown. The absorbent article 70 includes a liquid-permeable cover 76, a liquid-impermeable baffle 80 and an absorbent 81. The cover 76 encloses both the baffle 80 and the absorbent 81 and is overlapped upon itself on the garment-facing side of the article 70. The overlap is secured by a construction adhesive 78. A garment attachment adhesive 72 is secured to the exterior surface of the cover 76 approximate the overlap and, in turn, is covered by a removable peel strip 74. The absorbent 81 includes a pair of low density portions 82 and 84 which are integrally joined to a higher density portion 86. The lower density portions 82 and 84 are C-folded at junction lines (A) over the denser portion 86 and are aligned adjacent to the bodyside cover 76. A transfer layer 88 is positioned between the two less dense portions 82 and 84 and the dense portion 86. As explained above, the transfer layer 88 facilitates the movement of body fluid from the liquid-permeable cover 76 downward and outward to distant areas of the dense absorbent portion 86.

Figure 8:
FIG. 8 is a cross-sectional view of an absorbent material before it is compressed.
Figure 8A:
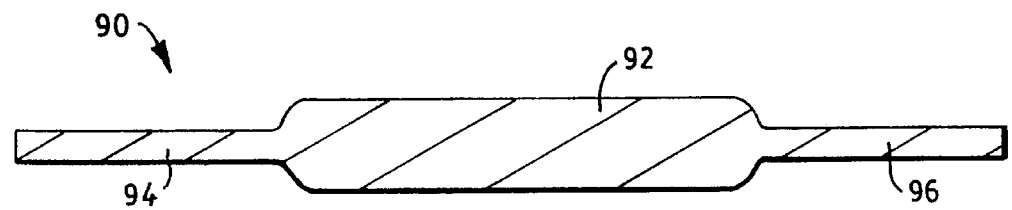
FIG. 8A is a cross-sectional view of a compressed absorbent material that can be used in the absorbent pad.

Referring to FIG. 8, an absorbent sheet 90 having a relatively low density is shown before compression. The absorbent sheet 90 has a homogeneous composition with an essentially constant density in the x, y and z directions. In FIG. 8A, an absorbent 91 is shown having a noncompressed center portion 92 flanked by a pair of compressed portions 94 and 96. The compressed portions 94 and 96 are located along the longitudinal sides of the center portion 92. The density of the compressed portions 94 and 96 is much greater than the noncompressed portion 92.

The density of the upper absorbent layer can be almost any desired value. This upper absorbent layer is soft and provides a cushiony feel adjacent to the wearer's skin. The upper absorbent layer also has good fluid transfer properties. A suitable density for the upper absorbent layer, which also acts as a transfer layer, has been found to be/between about 0.01 and about 0.07 grams per cubic centimeter. A preferred density for feminine care products has been found to be between about 0.02 and about 0.06 grams per cubic centimeter. This range is especially desirable when the material is coform which is made from a blend of 5–70% polypropylene and 95–30% divellicated wood fibers.

The density of the lower absorbent layer, which serves to stiffen and/or strengthen the product can be almost any desired value. The lower absorbent layer also functions as an absorbent reservoir which retains body fluids and prevents the fluid from being squeezed out when pressure is applied. It should be noted that the absorption properties of materials utilized for menstrual fluids are different from those for absorption of urine. A preferred density for feminine care products has been found to be between about 0.07 and about 0.30 grams per cubic centimeter. This range is especially desirable when the material is coform made from a blend of 30% polypropylene and 70% divellicated wood fibers. The thickness of the lower layer can also vary relative to the thickness of the upper layer. Preferably, the thickness of the lower layer is less than about 80% of the thickness of the upper layer. More preferably, the thickness of the lower layer is about 10–70% of the thickness of the upper layer and, most preferably, the thickness of the lower layer is about 15–50% of the thickness of the upper layer.

Figure 9:
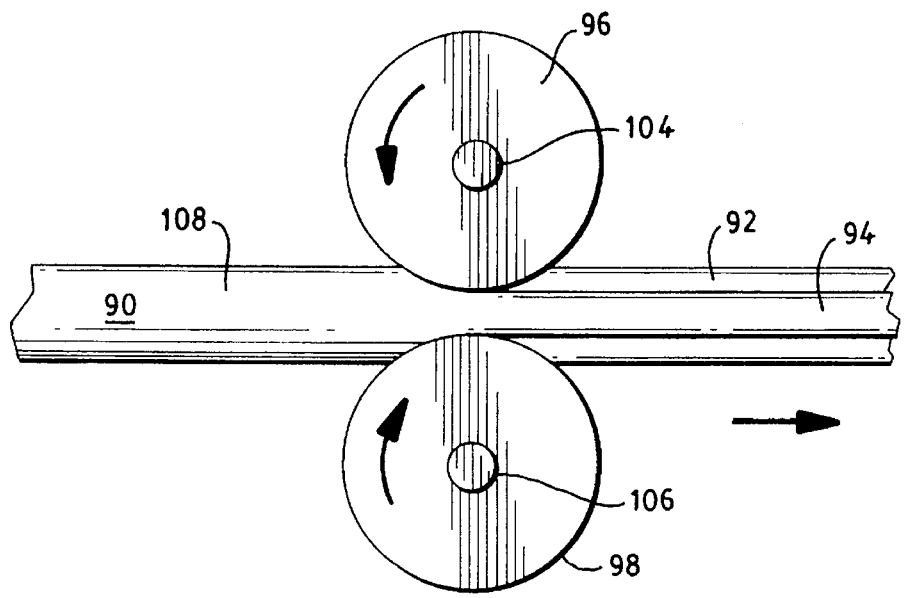
FIGS. 9 and 10 are side and end views, respectively, of apparatus which can compress the absorbent material.
Figure 10:
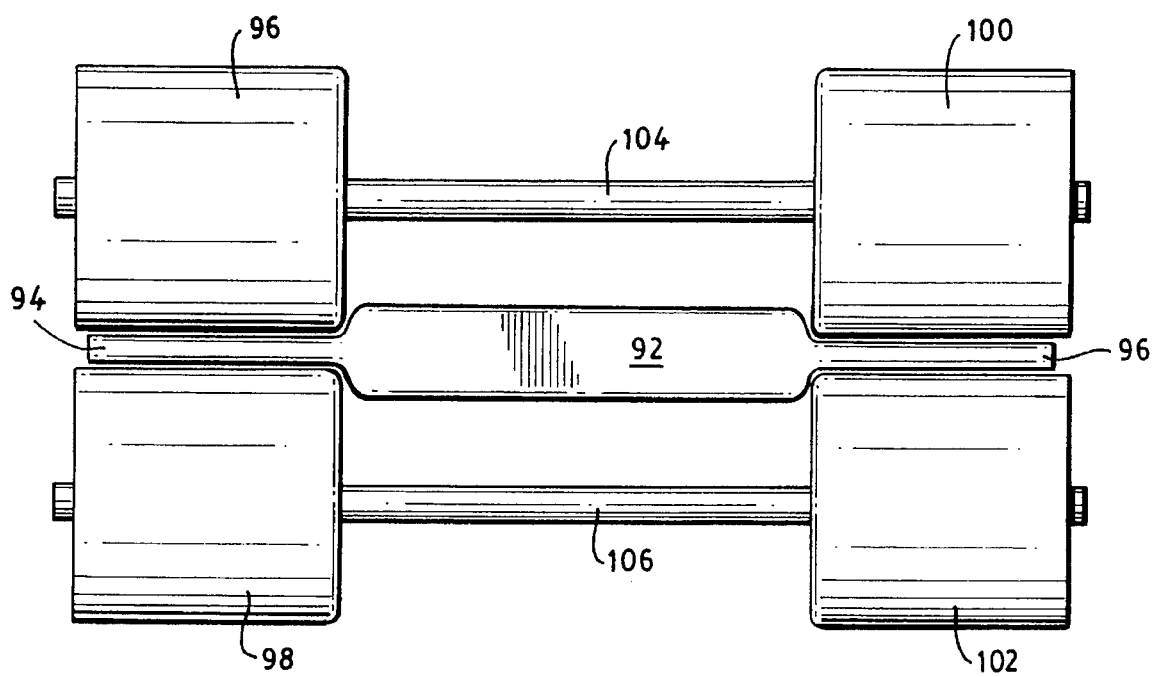

Referring to FIGS. 9 and 10, an apparatus is depicted for compressing the absorbent 90 into the configuration illustrated in FIG. 8A. The apparatus includes two pairs of rotatable pressure wheels or rolls 96 & 98 and 100 & 102. The pressure wheels 96 and 100 are mounted on an axle 104 while the pressure wheels 98 and 102 are mounted on an axle 106. The axles 104 and 106 are aligned parallel to one another and are rotatable by drive means (not shown). The noncompressed absorbent 90 is fed into a nip formed between the two pairs of pressure wheels 96 & 98 and 100 & 102. As the absorbent 90 passes between the nip formed by the pressure wheels 96 & 98 and 100 & 102, the compressed portions 94 and 96 are formed. The center portion 92 retains its original thickness since it was not subjected to any compression. The resulting configuration is absorbent 91 depicted in FIG. 8A.

Figure 11:
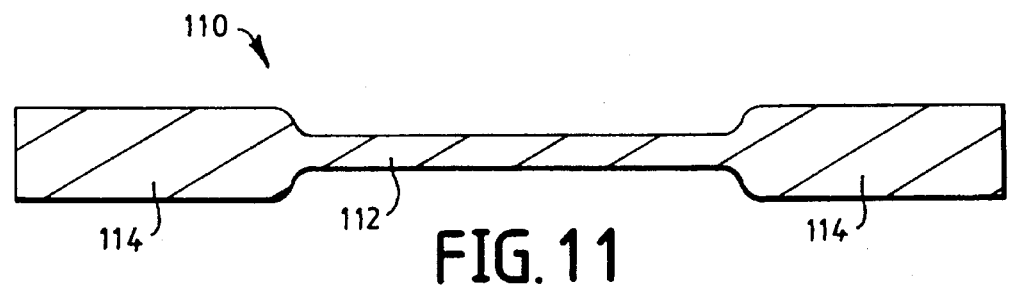
FIG. 11 is a cross-sectional view of an absorbent material which has been compressed and can be used in the absorbent pad.

Referring to FIG. 11, an absorbent 110 is shown having a compressed center portion 112 flanked by a pair of noncompressed or slightly compressed longitudinal end portions 114 and 115. An absorbent having this particular configuration could be used to form the absorbent article 70 shown in FIG. 7.

It should be noted that the pressure wheels 96, 98, 100 and 102 can be rearranged, be reduced in number, or be combined with additional pressure wheels to form other configurations. The method of forming an absorbent article can also vary depending on the desired configuration of the product. One preferred method includes compressing at least a portion of a sheet of absorbent having a homogeneous composition with an essentially constant density in any plane aligned perpendicular to the z direction into at least two distinct portions which have different thicknesses. The distinct portions should be integrally joined together by at least one junction line (A). The absorbent is folded on the junction line(s) (A) to obtain an upper layer and a lower layer. The overlying upper and lower layers provide a variable density in the z direction. An external surface of the lower layer is then heated to a sufficient temperature to fuse the surface and form a liquid-impermeable layer. A liquid-permeable cover can be positioned adjacent to the upper layer of the absorbent either during formation of the absorbent sheet or after the absorbent sheet has been compressed. It is also possible to position an extra layer of absorbent between the upper and lower layers of the folded absorbent to obtain the configuration shown in FIG. 7.

Another method includes compressing at least a portion of a sheet of absorbent material having a homogeneous composition with an essentially constant density in any plane aligned perpendicular to the z direction. The absorbent is compressed to form at least one compressed portion and at least one noncompressed portion. The compressed portion has a different thickness and a greater density than the noncompressed portion. The compressed portion and the noncompressed portion are integrally joined together by a junction line (A). The absorbent is then folded on the junction line (A) to vertically align the compressed portion with the noncompressed portion and create a variable density in the z direction. A liquid-permeable cover is positioned adjacent to a surface of the absorbent and a liquid-impermeable baffle is positioned adjacent to an opposite surface of the absorbent. The cover and the baffle are then secured together to enclose the absorbent.

Figure 12:
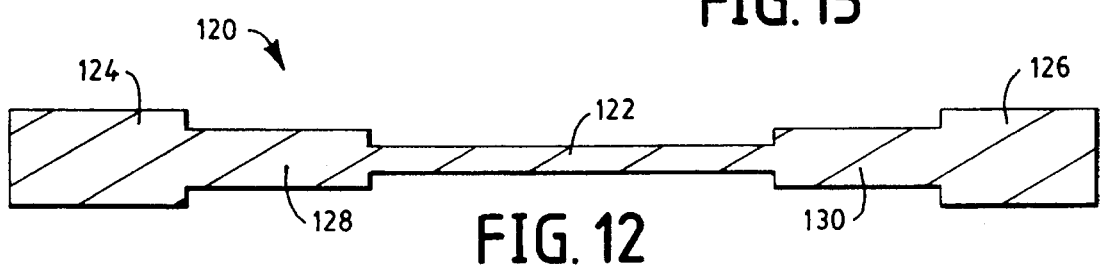
FIG. 12 is a cross-sectional view of an absorbent material which has been compressed to three different densities.

Referring to FIG. 12, an absorbent 120 having a more complicated configuration is shown. The absorbent 120 has three separate and distinct portions which are integrally joined together. Each portion has a different density and thickness. The absorbent 120 has a center portion 122 of greatest density and minimum thickness, a pair of longitudinal end portions 124 and 126 of lowest density and greatest thickness, and a pair of intermediate portions 128 and 130 each of which has a density greater than the center portion 122 but less than the end portions 124 and 126. The thickness of the intermediate portions 128 and 130 is less than the center portion 122 but greater than the end portions 124 and 126.

Figure 13:
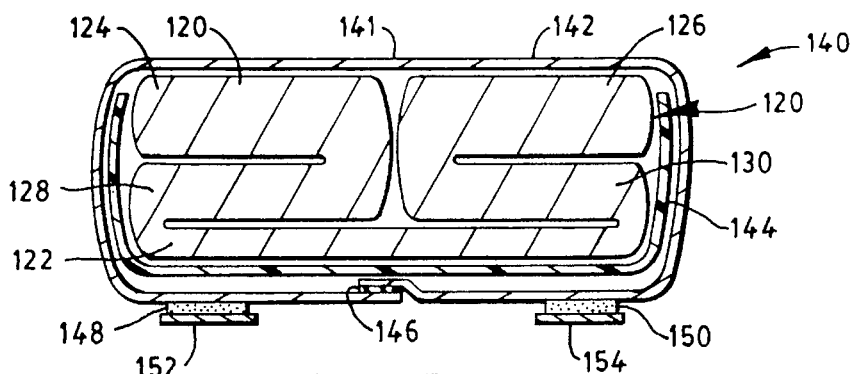
FIG. 13 is a cross-sectional view of an absorbent pad which has been formed from the compressed absorbent material shown in FIG. 12.

Referring to FIG. 13, an absorbent article 140 in the form of a sanitary napkin is shown utilizing the absorbent 120 illustrated in FIG. 12. The absorbent article 140 includes a liquid-permeable cover 142 having a bodyside surface 141. The cover 142 encloses both the absorbent 120 and a liquid-impermeable baffle 144 and is overlapped upon itself on the garment-facing surface or backside of the article 140. The overlap is secured by a construction adhesive 146. Two spaced-apart garment adhesive strips 148 and 150 are secured to the backside of the cover 142 and are protected by a pair of removable peel strips 152 and 154, respectively. The garment adhesive strips 148 and 150 are designed to hold the absorbent article 140 secure to the inner crotch portion of an undergarment when the article 140 is being worn.

In FIG. 13, the absorbent article 140 is formed with the absorbent 120 being folded in four places (A) and arranged with the lower density end portions 124 and 126 located adjacent to the cover 142. The intermediate dense portions 128 and 130 are located in the middle of the absorbent article 140 while the greatest density center portion 122 is located at the bottom, away from the body of the user. The low density portions 124 and 126 can be easily deformed with little resistance and, therefore, provides a soft feel against the thighs of the user.

Figure 14:
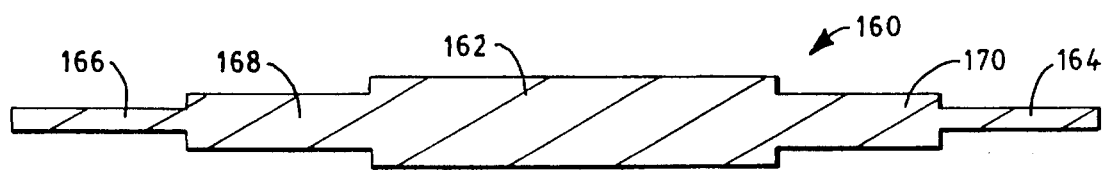
FIG. 14 is a cross-sectional view of an absorbent material which has been compressed to three different densities.

Referring to FIG. 14, another absorbent 160 is shown having a different configuration than that shown in FIG. 12. The absorbent 160 has three separate and distinct portions which are integrally joined together. Each portion has a different density and thickness. The absorbent 160 has a center portion 162 of greatest thickness but of lowest density, a pair of longitudinal end portions 164 and 166 of minimum thickness and greatest density, and a pair of intermediate portions 168 and 170 each of which has a density greater than the center portion 162 but less than the end portions 164 and 166. The thickness of the intermediate portions 168 and 170 is less than the center portion 162 but greater than the end portions 164 and 166.

Figure 15:
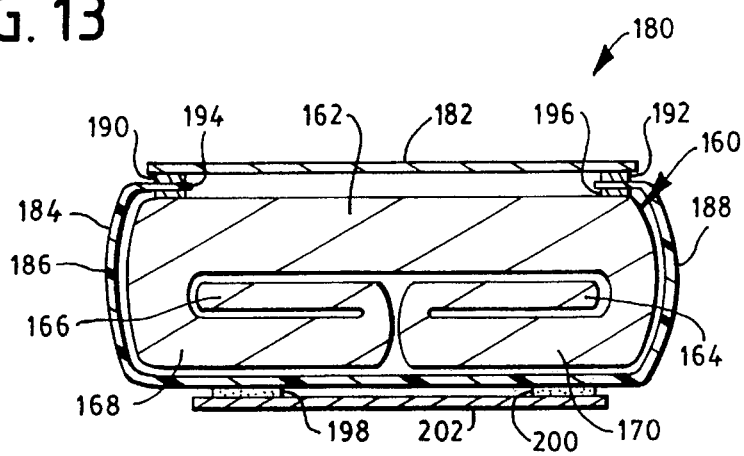
FIG. 15 is a cross-sectional view of an absorbent pad which has been formed from the compressed absorbent material shown in FIG. 14.

Referring to FIG. 15, an absorbent article 180 in the form of a sanitary napkin is shown utilizing the absorbent 160 illustrated in FIG. 14. The absorbent article 180 includes a liquid-permeable cover 182, the absorbent 160 and a liquid-impermeable baffle 184. The baffle 184 covers the lower surface of the absorbent 160 and also extends upwards and wraps around the sides of the absorbent 160 to form external sides 186 and 188 of the article 180. The baffle 184 terminates at the periphery of the upper surface of the absorbent 160. The cover 182 and the baffle 184 are joined together, for example, by a construction adhesive at locations 190 and 192 to completely enclose the absorbent 160. The attachment at 190 and 192 can be in the form of a continuous line of adhesive or it can include a plurality of intermittent glue spots. The baffle 184 is also attached to the absorbent 160 by a construction adhesive at locations 94 and 196. Again, the attachment at 194 and 196 can be in the form of a continuous line of adhesive or it can include a plurality of intermittent glue spots.

In FIG. 15, the absorbent article 180 is formed with the absorbent 160 being folded in four places (A). The high density end portions 164 and 166 are located in the center or middle of the article 180, the intermediate dense portions 168 and 170 are located adjacent to the lower surface of the absorbent article 180 and in contact with the baffle 184, and the low density portion 162 is located at the upper surface of the article 180 adjacent to the cover 182. The low density portion 162 can be easily deformed with little resistance and, therefore, provides a soft feel against the thighs of the user. The low density portion 162 has a large capillary structure which facilitates rapid transfer of body fluid from the bodyside cover 182 to the denser portions 164 and 166. The denser portions 164 and 166 have a smaller capillary structure which is capable of holding and retaining the body fluid. The dense portions 164 and 166 also provide transfer of body fluid in the longitudinal and transverse directions to the outer areas of the absorbent article 180. The intermediate dense portions 168 and 170 serve as storage areas for absorbed body fluid and provide strength to the absorbent article 180. The intermediate dense portions 168 and 170 also assist in preventing roping, bunching and twisting of the absorbent article 180 when it is being worn.

The absorbent article 180 also includes a pair of spaced-apart garment adhesive strips 198 and 200 which are secured to an exterior surface of the baffle 184 on the garment-facing side. The garment adhesive strips 198 and 200 are covered by a removable peel strip 202. The garment adhesive strips 198 and 200 are designed to hold the absorbent article 180 secure to the inner crotch portion of an undergarment when the article 180 is being worn.

Figure 16:
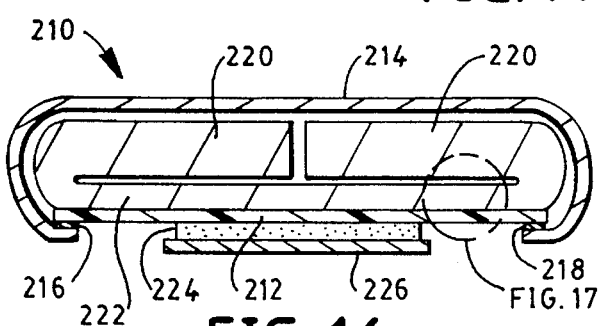
FIG. 16 is a cross-sectional view of an absorbent pad having a core formed from a compressed absorbent material and without a liquid-impermeable baffle.

Referring to FIG. 16, an absorbent article 210 in the form of a sanitary napkin is shown. The absorbent article 210 includes a liquid-permeable cover 214 and an absorbent 215 which has an integrally formed liquid-impermeable layer 212. The liquid-impermeable layer 212 serves as a baffle and will prevent the passage of body fluid therethrough. The liquid-impermeable layer 212 can be formed by heating a surface of the absorbent 215 during the compression step such that a more dense layer or skin is obtained. By subjecting the absorbent to sufficient heat and pressure, one can make at least one surface of the absorbent substantially liquid impermeable. The liquid-impermeable layer 212 is adhesively secured to the cover 214 at locations 216 and 218. The attachment at 216 and 218 can be in the form of a continuous line of adhesive or it can include a plurality of intermittent glue spots.

The absorbent 215 is an integral sheet of absorbent having a high density portion 222 flanked by a pair of low density portions 220 and 221. In the formation of the absorbent article 210, the absorbent 215 is C-folded at (A) such that the two low density portions 220 and 221 are positioned toward the upper surface of the article 210 adjacent to the cover 214. The higher density portion 222 is located beneath the low density portions 220 and 221 and adjacent to the garment-facing surface of the article 210. The garment-facing surface is designed to contact the inner crotch portion of an undergarment.

The absorbent article 210 also includes a garment adhesive strip 224 secured to the liquid-impermeable layer 212 along the longitudinal central axis of the article 210. The adhesive strip 224 is covered by a removable peel strip 226. The peel strip 226 prevents the adhesive strip 224 from being contaminated by foreign debris. When the sanitary napkin 210 is ready to be worn, the wearer will remove the peel strip 226 and attach the napkin to the inner surface of her undergarment via the garment adhesive strip 224.

Figure 17:
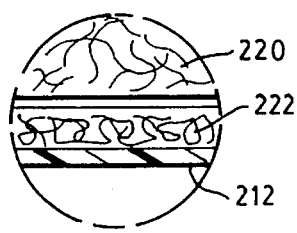
FIG. 17 is an enlarged view of a portion of the absorbent pad shown in FIG. 16.

Referring to FIG. 17, an enlarged view of a portion of the absorbent article 210 is shown which emphasizes the integral formation of the liquid-impermeable layer 212 and the high dense portion 222. As explained above, the liquid-impermeable layer 212 can be formed by heating a surface of the absorbent 210 during compression such that a polymer layer is formed. In reference to the equipment shown in FIG. 10, the pressure wheels 98 and 102 can be heated to an elevated temperature to enable the fibers at the surface of the absorbent to fuse together while the pressure wheels 96 and 100 would be maintained at room temperature or at a lower temperature so that fusing does not occur.

Figure 18:
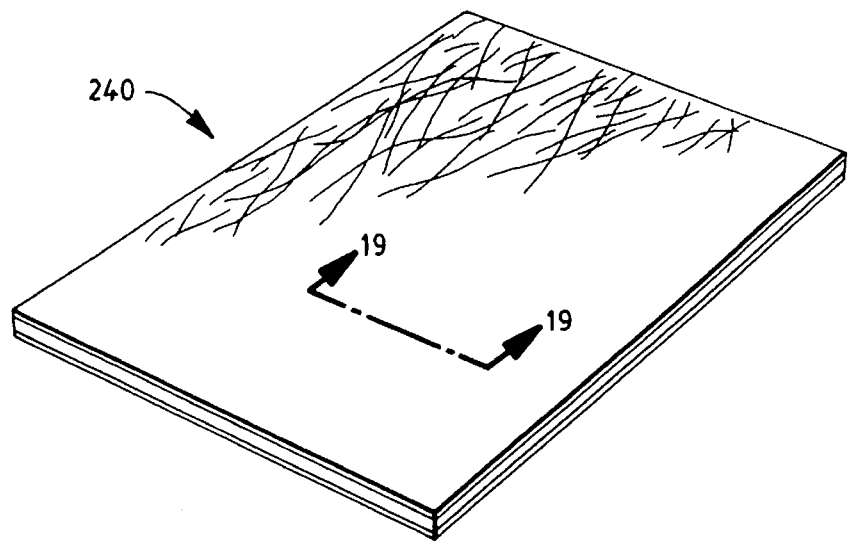
FIG. 18 is a perspective view of a bedpad utilizing a compressed absorbent material.
Figure 19:
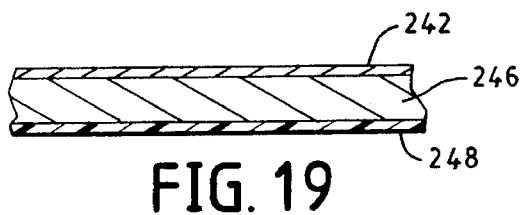
FIG. 19 is a cross-sectional view of a portion of the bedpad taken along line 19—19 of FIG. 18.

Referring to FIGS. 18 and 19, a bedpad 240 is shown which includes a liquid-permeable cover 242, an absorbent 246 and a liquid-impermeable baffle 248. The absorbent 246 can be formed from a sheet of coform. Such a material is ordinarily formed on a substrate, such as a liquid-permeable spunbond material, that may serve as the cover 242. It should be noted that the liquid-permeable cover 242 and the liquid-impermeable baffle 248 can be integrally formed with the absorbent 246 if desired. The cover 242 and the baffle 248 can be formed at the same time the absorbent 246 is being manufactured into a sheet. This can be accomplished by laying down a spunbond material on a forming wire and then depositing coform on the spunbond material. The combination is then directed through the nip of a pair of compression rollers. One of the compression rollers can be heated to an elevated temperature which will cause the fibers at the surface of the coform to fuse together while being compressed. This fused layer can form the baffle 248 while the opposite spunbond layer can form the cover 242. It should be noted that the absorbent 246 can also be compressed by using platen presses in an intermittent process.

Figure 20:
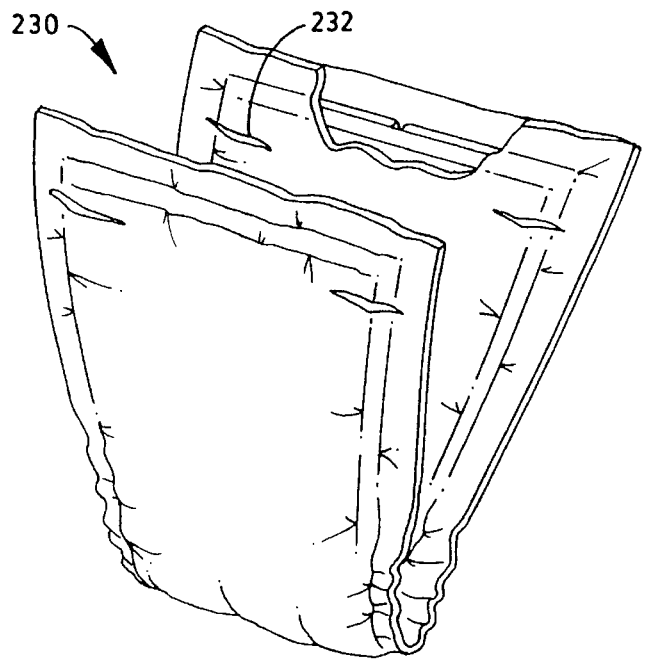
FIG. 20 is a perspective view with a portion cut away, of an incontinent garment utilizing a compressed absorbent material.

Referring to FIG. 20, an absorbent article 250 in the form of an incontinent garment is shown. The incontinent garment 250 contains four buttonholes 252 which are used for the insertion of elastic straps having a button attached to each end. A button is inserted through each buttonhole 252 and the elastic straps serve to hold the incontinent garment 250 about the wearer's torso. The present invention can also be used in connection with other types of incontinence garments that are held in place by garment adhesive strips which attach directly to an undergarment.

Figure 21:
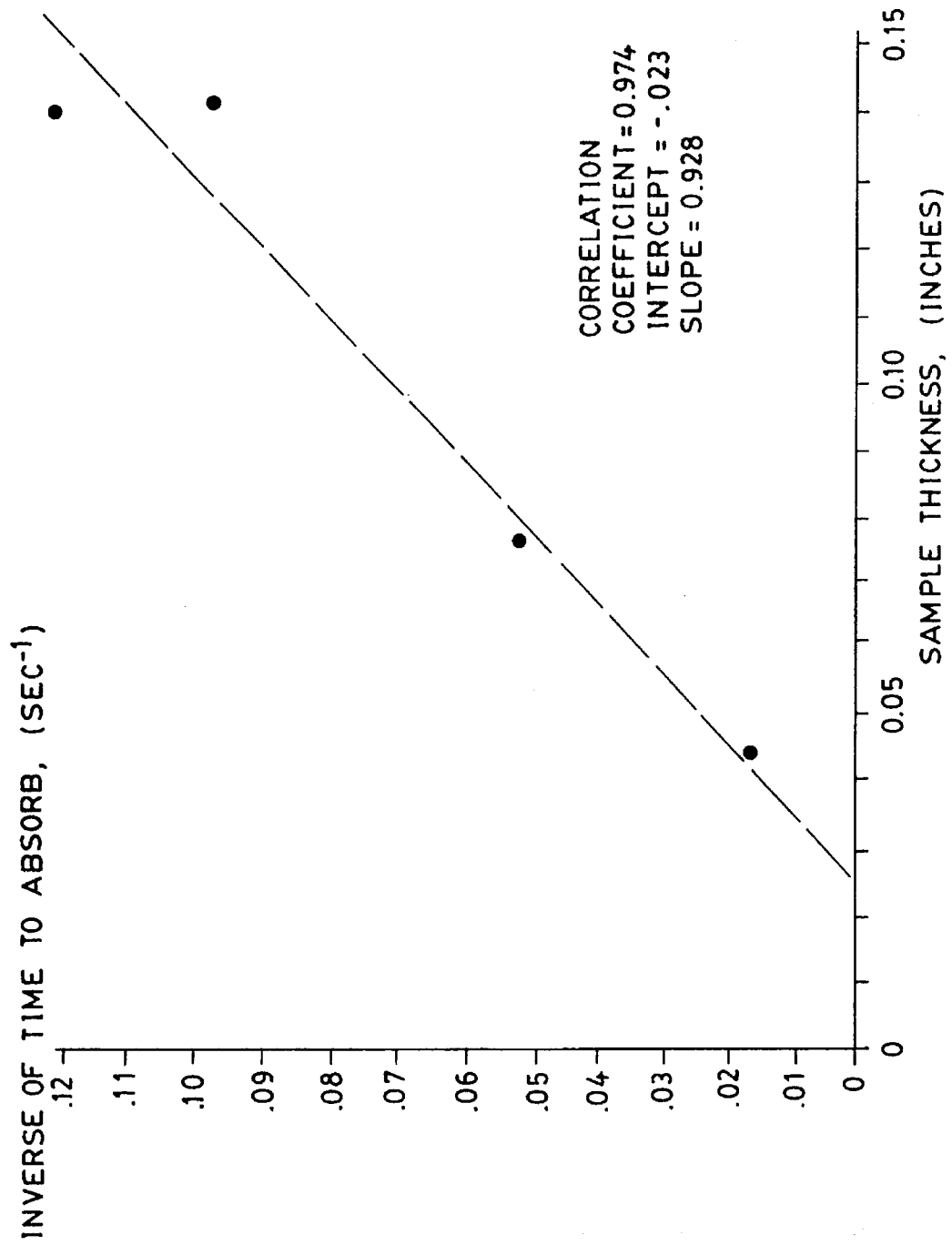
FIG. 21 is a graph depicting the inverse of the time required to absorb fluid (in seconds) versus the thickness of the sample (in inches).

Lastly, referring to FIG. 21, a graph is depicted plotting the "thickness" of each sample in inches along the x axis and the "inverse of the time to absorb the fluid" in seconds along the y axis.

EXAMPLES

The following examples are intended to be illustrative of the invention.

A sheet of commercially produced 190 gram per square meter coform material containing 70% pulp and 30% meltblown polypropylene microfibers with some TRITON X-102 wetting agent was used in all of the following examples. The coform was formed on a spunbond carrier sheet which had a basis weight of about 22 grams per square meter. The meltblown insert, where used, had a basis weight of 2.65 oz./square yard (90 grams/square meter) and comprised a 6 inch square sheet which was folded four times. The meltblown insert was inserted into the folded absorbent article and it had a dimension of 1½ inches wide by 6 inches long. It was placed in the center of the absorbent article.

EXAMPLE 1—Uncompressed Control

A sheet of the above-described coform was not compressed but was used as received. Six samples were cut from the sheet. They were 6 inches long and 12 inches wide. The samples were divided into four quarters, each quarter being 1½ inches wide by 12 inches long. The left, two centers, and right quadrants were measured for thickness with a DYER GAUGE, Model number 9.210–026. The thickness of each sample was reported as sample numbers 1–6 on Table 1 and are identified as "uncompressed" samples. The "average sample thickness" values for each of the four Example groups (Examples 1, 2, 3 and 4) of the six samples in the left, center and right locations are reported in Table 2. The material was folded at the left and right quadrant lines to form an absorbent article, such as that shown in FIG. 5, except that it had an absorbent with a uniform density in the x, y and z directions. The tests results are reported in Tables 3 and 4.

EXAMPLE 2—Uniformly Compressed

A sheet of the above-described coform was cut into six samples as explained above and were uniformly compressed in a CARVER LABORATORY PRESS, Model No. 2518. This equipment is available from Fred S. Carver, Inc., Menomonee Falls, Wis. A spacer was placed next to the samples so that they were only partially compressed. The measured thickness (after partial compression) for the left and right quadrants and center one-half is listed in Table 1 as sample numbers 8–13 and are identified as "uniformly compressed" samples. The "average sample thickness" values at the left, center and right locations are reported in Table 2. The test results are reported in Tables 3 and 4.

Example 3—Compressed Edges

A sheet of the above-described coform was cut into six samples as explained in Example 1. Each sample was compressed only at the left and right quadrants. The thickness of each sample was measured as described above and is reported in Table 1 as sample numbers 14–19 and are identified as "compressed edges" samples. The "average sample thickness" values are reported in Table 2 and the test results are reported in Tables 3 and 4.

EXAMPLE 4—Compressed Center

A sheet of the above-described coform was cut into six samples as explained in Example 1. Each sample was compressed only in the center two quadrants by putting a metal plate over only the area to be compressed. When the platens of the press were brought together, pressure was applied on the coform only where the thick metal plate was positioned over the center two quadrants of the material so the left and right quadrants of the material remained uncompressed. The thickness of each sample was measured as described above and is reported in Table 1 as sample numbers 20–25 and are identified as "compressed center" samples. The "average sample thickness" values are reported in Table 2 and the test results are reported in Tables 3 and 4.

Test Results

The time in seconds required to absorb eight milliliters of 30% red blood cell bovine blood is reported in Table 3. Sample articles were run with and without meltblown inserts as listed in Table 3. As the time to absorb did not appear to be greatly affected by the presence or absence of the meltblown insert, all time numbers were averaged for each coform type and are reported in Column 3, "overall average time (seconds)", with "standard deviations" in Column 4. As predicted, the time to absorb for the "uncompressed" and "compressed edges" samples was about the same at 10.4 seconds and 8.3 seconds, respectively. In both examples, the center absorbing coform was uncompressed. The "moderately densified" samples and the "uniformly compressed" samples had an absorbency time of almost 20 seconds while the samples with the "compressed center" portions, where the absorbency was being evaluated, had an absorbency time in excess of 60 seconds. A plot of the "sample thickness" versus "the inverse of the time to absorb the fluid" is shown in FIG. 21.

Test articles were also evaluated on the "blood wicker" test not using a meltblown insert.

The "blood wicker" test involved the supply of 30% red blood cell bovine blood at 37° C. at a flow rate of three grams per hour for three hours to the absorbent article. The articles were then removed from the test stand and a blotter was placed on top of them. One pound per square inch (psi) of pressure was applied to the top of the blotter for three minutes. The blotter was then removed and weighed to determine the amount of fluid that could be wicked out of the top of the article. The value was reported as the percentage by weight of the fluid that went back into the blotter versus the weight of fluid applied to the article. A low percentage value indicated a drier feeling article. It is readily apparent from Table 4 that the samples with the "compressed edges" had the lowest rewet value at 8.4% versus 22.4%, 26.2% and 27.5% for the other three article constructions.

The thickness of the four different article constructions without a meltblown insert can be estimated from Table 2 by adding the thickness of the center portion and the average thickness of the right and left edges. Thus, the thickness of an article made from the "uncompressed" sample would be 0.142+(0.144+0.143)/2=0.286 inches. The thickness of an article made from the "uniformly compressed" sample would be 0.154 inches. The thickness of an article made from the "compressed edges" would be 0.173 inches. Lastly, thickness of an article made from the "compressed center" would be 0.195 inches.

Accordingly, samples having "compressed edges" retained the desired thinness for comfort and discreetness while maintaining a soft, uncompressed material next to the body for comfort and rapid fluid absorbency. The "compressed edges," which form the bottom layer of the article when "C" folded into an absorbent article, act as a fluid-wicking material and reservoir to ensure a dry surface next to the skin of the wearer.

TABLE 1

| Sample Number | Sample Identification | Sample Thickness (in Inches) | | |
|---|---|---|---|---|
| | | Left | Center | Right |
| 1 | Uncompressed (Ex. #1) | .133 | .140 | .138 |
| 2 | " | .139 | .158 | .134 |
| 3 | " | .135 | .135 | .150 |

TABLE 1-continued

| Sample Number | Sample Identification | Sample Thickness (in Inches) | | |
|---|---|---|---|---|
| | | Left | Center | Right |
| 4 | " | .164 | .130 | .144 |
| 5 | " | .152 | .144 | .144 |
| 6 | " | .144 | .145 | .146 |
| 8 | Uniformly Compressed (Ex. #2) | .064 | .068 | .075 |
| 9 | " | .065 | .068 | .079 |
| 10 | " | .083 | .077 | .082 |
| 11 | " | .066 | .074 | .072 |
| 12 | " | .089 | .085 | .080 |
| 13 | " | .094 | .086 | .086 |
| 14 | Compressed Edges (Ex. #3) | .030 | .042 | .031 |
| 15 | " | .032 | .142 | .034 |
| 16 | " | .034 | .139 | .032 |
| 17 | " | .031 | .131 | .031 |
| 18 | " | .033 | .146 | .030 |
| 19 | " | .034 | .147 | .031 |
| 20 | Compressed Center (Ex. #4) | .159 | .035 | .149 |
| 21 | " | .139 | .042 | .167 |
| 22 | " | .149 | .045 | .162 |
| 23 | " | .153 | .044 | .147 |
| 24 | " | .151 | .047 | .143 |
| 25 | " | .149 | .050 | .146 |

Note: "Number 7" was not used to identify any sample.

TABLE 2

| Sample Identification | Average Sample Thickness (in Inches) | | | | | |
|---|---|---|---|---|---|---|
| | Left | | Center | | Right | |
| Uncompressed (Ex. #1) | 0.144 | 0.08 | 0.142 | 0.010 | 0.143 | 0.006 |
| Uniformly compressed (Ex. #2) | 0.077 | 0.013 | 0.076 | 0.008 | 0.079 | 0.005 |
| Compressed edges (Ex. #3) | 0.0323 | 0.002 | 0.141 | 0.006 | 0.0315 | 0.001 |
| Compressed center (Ex. #4) | 0.150 | 0.007 | 0.044 | 0.005 | 0.152 | 0.010 |

Note: All thickness measurements taken with a DYER GAUGE Model #9.210-026

TABLE 3

| | 8 Milliliter Absorbency Time (in Seconds) | | | |
|---|---|---|---|---|
| Coform Type | Without Meltblown Insert | With Meltblown Insert | Overall Average Time, (Sec.) | Standard Deviation (Sec.) |
| Uncompressed (Ex. #1) | 13.4, 11.6 7.8, 6.3 11.1, 9.1 | 10.4, 12.3 12.7, 10.4 8.9 | 10.4 | 2.1 |
| Uniformly compressed (Ex. #2) | 12.3, 12.3 10.6, 25.9 9.11 | 18.6, 29.7 26.8, 31.3 18.6, 18.2 | 19.4 | 7.6 |
| Compressed edges (Ex. #3) | 6.5, 4.7 3.9, 5.2 5.8 | 9.1, 6.0 8.7, 7.0 (52.0*) 25.7 | 8.3 | 6.0 |
| Compressed center (Ex. #4) | 106.4, 52.8 113.9 | 52.2, 36.6 108.4, 22.3 27.2 | 65.0 | 36.0 |

*Reading not used in average value; value over seven standard deviations from the mean.

TABLE 4

Blotter Rewet Values
Without Meltblown Inserts

| Coform Type | Total Bovine Blood Delivered, Grams | Blotter Rewet 1 psi Value, grams | Rewet % | Average Rewet % | Standard Deviation % |
|---|---|---|---|---|---|
| Un- compressed (Ex. #1) | 9.29 | 2.05 | 22.1 | 22.4 | 2.2 |
|  | 8.85 | 1.77 | 20.0 |  |  |
|  | 9.46 | 2.39 | 25.3 |  |  |
| Uniformly compressed (Ex. #2) | 8.33 | 2.37 | 28.4 | 26.2 | 1.6 |
|  | 8.71 | 2.21 | 25.4 |  |  |
|  | 8.70 | 2.16 | 24.8 |  |  |
| Com- pressed edges (Ex. #3) | 8.66 | 0.66 | 7.6 | 8.4 | 2.2 |
|  | 9.09 | 1.03 | 11.3 |  |  |
|  | 8.97 | 0.55 | 6.1 |  |  |
| Com- pressed center (Ex. #4) | 8.60 | 12.91 | 22.2 | 27.5 | 4.1 |
|  | 8.66 | 2.78 | 32.1 |  |  |
|  | 8.80 | 2.49 | 28.3 |  |  |

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. A method of forming an absorbent article for absorbing fluid, comprising the steps of:
   a) compressing a sheet of absorbent into at least two compressed portions which are integrally joined to at least one noncompressed portion at two junction lines, each portion having a different thickness;
   b) folding said absorbent at each of said junction lines to vertically align said compressed portions with said noncompressed portion to create a variable density in the z direction;
   c) heating an external surface of at least one of said compressed portions to a sufficient temperature to fuse said surface and form a liquid-impermeable layer; and
   d) enclosing said absorbent with a liquid-permeable cover.

* * * * *